US012667705B2

(12) United States Patent　　(10) Patent No.:　US 12,667,705 B2
Ben-Tsur　　(45) Date of Patent:　Jun. 30, 2026

(54) VIBRATING CAPSULE FOR ENHANCING ABSORPTION OF INGESTED MEDICAMENTS

(71) Applicant: Vibrant Ltd., Yokneam (IL)

(72) Inventor: Lior Ben-Tsur, Netanya (IL)

(73) Assignee: Vibrant Ltd., Yokneam (IL)

( * ) Notice: Subject to any disclaimer, the term of this patent is extended or adjusted under 35 U.S.C. 154(b) by 1114 days.

(21) Appl. No.: 17/044,258

(22) PCT Filed: Apr. 8, 2019

(86) PCT No.: PCT/IB2019/052866
§ 371 (c)(1),
(2) Date: Oct. 1, 2020

(87) PCT Pub. No.: WO2019/197964
PCT Pub. Date: Oct. 17, 2019

(65) Prior Publication Data
US 2021/0023357 A1　Jan. 28, 2021

Related U.S. Application Data

(63) Continuation-in-part of application No. 16/185,044, filed on Nov. 9, 2018, now Pat. No. 10,543,348, and
(Continued)

(51) Int. Cl.
*A61M 37/00*　(2006.01)
*A61M 31/00*　(2006.01)

(52) U.S. Cl.
CPC ...... *A61M 37/0092* (2013.01); *A61M 31/002* (2013.01); *A61M 2205/3306* (2013.01);
(Continued)

(58) Field of Classification Search
CPC ............ A61M 37/0092; A61M 31/002; A61M 2205/3306; A61M 2205/3331; A61M 2205/3368; A61M 2210/1053
See application file for complete search history.

(56) References Cited

U.S. PATENT DOCUMENTS 3,485,235 A　12/1969　Felson
4,507,115 A　　3/1985　Kambara et al.
(Continued)

FOREIGN PATENT DOCUMENTS

CN　　　1829466 A　　9/2006
CN　　102743174 A　　10/2012
(Continued)

OTHER PUBLICATIONS

'Smart capsule to target colon diseases', Ben Gruber, Sep. 30, 2015 https://www.reuters.com/article/us-smart-capsule-colon-idUSKCNORU1ZE20150930.
(Continued)

*Primary Examiner* — Bhisma Mehta
*Assistant Examiner* — Mark A Igel
(74) *Attorney, Agent, or Firm* — Momentum IP Ltd.; Marc Van Dyke

(57) ABSTRACT

A system and a method of using a vibrating gastrointestinal capsule in coordination with an ingestible medicament. The vibrating gastrointestinal capsule may include a housing; a vibrating agitation mechanism causing said housing to exert vibrations on an environment surrounding the vibrating gastrointestinal capsule; a power supply for powering said vibrating agitation mechanism; and a control mechanism for activating said vibrating agitation mechanism to operate in said vibration mode of operation, such that the vibration mode of operation at least partially transpires or completely transpires within an actual or estimated absorption time
(Continued)

period of the ingestible medicament within the gastrointestinal tract of the subject.

13 Claims, 2 Drawing Sheets

Related U.S. Application Data a continuation-in-part of application No. 16/178,425, filed on Nov. 1, 2018, now Pat. No. 10,537,720.

(60) Provisional application No. 62/655,031, filed on Apr. 9, 2018.

(52) U.S. Cl.
CPC .............. *A61M 2205/3331* (2013.01); *A61M 2205/3368* (2013.01); *A61M 2210/1053* (2013.01)

(56) References Cited

U.S. PATENT DOCUMENTS

| | | | |
|---|---|---|---|
| 4,692,324 A * | 9/1987 | Davis ................. A61K 51/1203 424/1.61 |
| 5,170,801 A | 12/1992 | Casper et al. |
| 6,632,216 B2 | 10/2003 | Houzego et al. |
| 6,776,165 B2 | 8/2004 | Jin |
| 6,929,363 B2 | 8/2005 | Sakai et al. |
| 6,984,205 B2 | 1/2006 | Gazdzinski |
| 8,202,697 B2 | 6/2012 | Holmes |
| 8,518,022 B2 | 8/2013 | Trovato et al. |
| 8,597,278 B2 | 12/2013 | Trovato et al. |
| 8,701,677 B2 | 4/2014 | Duan et al. |
| 9,078,799 B2 | 7/2015 | Shohat et al. |
| 9,156,169 B2 | 10/2015 | Duan et al. |
| 9,232,909 B2 | 1/2016 | Duan et al. |
| 9,532,923 B2 | 1/2017 | Shohat et al. |
| 9,707,150 B2 | 7/2017 | Shabbat |
| 10,537,720 B2 * | 1/2020 | Ben-Tsur ........... A61K 41/0023 |
| 10,543,348 B2 | 1/2020 | Ben-Tsur |
| 10,814,113 B2 * | 10/2020 | Ben-Tsur ................. A61B 5/01 |
| 10,888,277 B1 * | 1/2021 | Ben-Tsur ................. A61H 1/00 |
| 10,905,378 B1 | 2/2021 | Ben-Tsur |
| 11,020,018 B2 | 6/2021 | Ben-Tsur |
| 11,052,018 B2 | 7/2021 | Molnar |
| 11,197,798 B2 | 12/2021 | Shohat |
| 11,478,401 B2 | 10/2022 | Ben-Tsur |
| 11,504,024 B2 | 11/2022 | Ben-Tsur |
| 11,510,590 B1 | 11/2022 | Ben-Tsur |
| 11,638,678 B1 * | 5/2023 | Ben-Tsur .............. A61H 21/00 601/46 |
| 2002/0132226 A1 | 9/2002 | Nair et al. |
| 2003/0020810 A1 | 1/2003 | Takizawa et al. |
| 2004/0030454 A1 | 2/2004 | Kim et al. |
| 2004/0253304 A1 | 12/2004 | Gross et al. |
| 2004/0267240 A1 | 12/2004 | Gross et al. |
| 2005/0058701 A1 | 3/2005 | Gross et al. |
| 2005/0085696 A1 | 4/2005 | Uchiyama et al. |
| 2005/0148847 A1 | 7/2005 | Uchiyama et al. |
| 2005/0177069 A1 * | 8/2005 | Takizawa ............. A61B 5/0084 600/573 |
| 2006/0169293 A1 | 8/2006 | Yokoi et al. |
| 2006/0276729 A1 | 12/2006 | Reed et al. |
| 2007/0015952 A1 | 1/2007 | Chang et al. |
| 2007/0238940 A1 | 10/2007 | Amirana |
| 2008/0188837 A1 * | 8/2008 | Belsky ................. A61K 9/0097 604/890.1 |
| 2008/0275430 A1 | 11/2008 | Belsky et al. |
| 2009/0281380 A1 | 11/2009 | Miller et al. |
| 2009/0306633 A1 | 12/2009 | Trovato et al. |
| 2009/0318841 A1 * | 12/2009 | Shohat .............. A61H 23/0263 601/46 |
| 2010/0049012 A1 | 2/2010 | Dijksman et al. |
| 2010/0217079 A1 | 8/2010 | Tichy |
| 2013/0267788 A1 | 10/2013 | Duan et al. |
| 2015/0011829 A1 | 1/2015 | Wang et al. |
| 2015/0018614 A1 | 1/2015 | Duan et al. |
| 2015/0018615 A1 | 1/2015 | Duan et al. |
| 2015/0073315 A1 * | 3/2015 | Shabbat ............. A61H 23/0254 601/46 |
| 2015/0313792 A1 | 11/2015 | Shohat |
| 2015/0380140 A1 | 12/2015 | Duan et al. |
| 2016/0136104 A1 * | 5/2016 | Niichel .............. A61K 41/0028 424/452 |
| 2016/0287058 A1 | 10/2016 | Ye et al. |
| 2016/0303133 A1 | 10/2016 | Dudley |
| 2016/0310357 A1 | 10/2016 | Duan et al. |
| 2017/0020374 A1 | 1/2017 | Duan et al. |
| 2017/0035407 A1 | 2/2017 | Duan et al. |
| 2017/0035520 A1 | 2/2017 | Duan et al. |
| 2017/0135897 A1 | 5/2017 | Shohat et al. |
| 2017/0273863 A1 | 9/2017 | Shabbat |
| 2017/0296425 A1 * | 10/2017 | Duan ..................... A61H 23/02 |
| 2017/0296428 A1 | 10/2017 | Duan et al. |
| 2017/0340242 A1 | 11/2017 | Duan |
| 2018/0055597 A1 | 3/2018 | Duan et al. |
| 2018/0084975 A1 | 3/2018 | Duan et al. |
| 2019/0224070 A1 | 7/2019 | Ben-Tsur |
| 2019/0307999 A1 | 10/2019 | Ben-Tsur |
| 2019/0308002 A1 | 10/2019 | Ben-Tsur |
| 2020/0214592 A1 | 7/2020 | Ben-Tsur |
| 2020/0229733 A1 | 7/2020 | Ben-Tsur |
| 2020/0246216 A1 | 8/2020 | Molnar |
| 2020/0315541 A1 | 10/2020 | Ben-Tsur |
| 2021/0023357 A1 | 1/2021 | Ben-Tsur |
| 2021/0066998 A1 | 3/2021 | Molnar |
| 2021/0196296 A1 | 7/2021 | Ben-Tsur |
| 2021/0236381 A1 | 8/2021 | Ben-Tsur |
| 2021/0290483 A1 | 9/2021 | Molnar |
| 2021/0322741 A1 * | 10/2021 | Ben-Tsur .......... A61M 5/14276 |
| 2021/0386316 A1 | 12/2021 | Ben-Tsur |
| 2022/0054352 A1 | 2/2022 | Shohat |
| 2022/0111187 A1 | 4/2022 | Ben-Tsur |
| 2022/0409139 A1 | 12/2022 | Ben-Tsur |
| 2023/0059127 A1 | 2/2023 | Ben-Tsur |
| 2023/0104338 A1 | 4/2023 | Ben-Tsur |

FOREIGN PATENT DOCUMENTS

| | | |
|---|---|---|
| CN | 102743175 A | 10/2012 |
| CN | 102743176 A | 10/2012 |
| CN | 202483565 U | 10/2012 |
| CN | 102813515 A | 12/2012 |
| CN | 102860810 A | 1/2013 |
| CN | 202699138 U | 1/2013 |
| CN | 202821355 U | 3/2013 |
| CN | 202843564 U | 4/2013 |
| CN | 202843608 U | 4/2013 |
| CN | 202875332 U | 4/2013 |
| CN | 103222842 A | 7/2013 |
| CN | 203634116 U | 6/2014 |
| CN | 104898850 A | 9/2015 |
| CN | 105025245 A | 11/2015 |
| CN | 105079970 A | 11/2015 |
| CN | 105411505 A | 3/2016 |
| CN | 205108749 U | 3/2016 |
| CN | 105939451 A | 9/2016 |
| CN | 105942959 A | 9/2016 |
| CN | 105996961 A | 10/2016 |
| CN | 106056588 A | 10/2016 |
| CN | 106097335 A | 11/2016 |
| CN | 106137760 A | 11/2016 |
| CN | 106204599 A | 12/2016 |
| CN | 205758500 U | 12/2016 |
| CN | 106373137 A | 2/2017 |
| CN | 205913317 U | 2/2017 |
| CN | 205928774 U | 2/2017 |
| CN | 106923787 A | 7/2017 |
| CN | 106934799 A | 7/2017 |
| CN | 107174188 A | 9/2017 |
| CN | 107233580 A | 10/2017 |
| CN | 107240091 A | 10/2017 |

(56)                References Cited

FOREIGN PATENT DOCUMENTS

| CN | 107375951 A | 11/2017 |
| EP | 2987447 A1 | 2/2016 |
| EP | 2995240 A1 | 3/2016 |
| JP | 2001062397 A | 3/2001 |
| JP | 2010503451 A | 2/2010 |
| WO | 2006025013 A1 | 3/2006 |
| WO | 2007013059 A2 | 2/2007 |
| WO | 2008012700 A1 | 1/2008 |
| WO | 2008035329 A2 | 3/2008 |
| WO | 2009063375 A1 | 5/2009 |
| WO | 2013121276 A1 | 8/2013 |
| WO | 2018055487 A1 | 3/2018 |

OTHER PUBLICATIONS

'Advanced Delivery Devices—IntelliCap: An Intelligent, Electronic Capsule for Oral Drug Delivery & Development', Drug Development & Delivery, Apr. 2013 http://drug-dev.com/advanced-delivery-devices-intellicap-an-intelligent-electronic-capsule-for-oral-drug-delivery-development/.
Machine Translation (by Google Patents) for CN 102743174 published on Oct. 24, 2012.
Machine Translation (by Google Patents) for CN 102743175 published on Oct. 24, 2012.
Machine Translation (by Google Patents) for CN 102743176 published on Oct. 24, 2012.
Machine Translation (by Google Patents) for CN 102813515 published on Dec. 12, 2012.
Machine Translation (by Google Patents) for CN 102860810 published on Jan. 9, 2013.
Machine Translation (by Google Patents) for CN 03222842 published on Jul. 31, 2013.
Machine Translation (by Google Patents) for CN 104898850 published on Sep. 9, 2015.
Machine Translation (by Google Patents) for CN 105025245 published on Nov. 4, 2015.
Machine Translation (by Google Patents) for CN 105079970 published on Nov. 25, 2015.
Machine Translation (by Google Patents) for CN 105411505 published on Mar. 23, 2016.
Machine Translation (by Google Patents) for CN 105939451 published on Sep. 14, 2016.
Machine Translation (by Google Patents) for CN 105942959 published on Sep. 21, 2016.
Machine Translation (by Google Patents) for CN 105996961 published on Oct. 12, 2016.
Machine Translation (by Google Patents) for CN 106056588 published on Oct. 26, 2016.
Machine Translation (by Google Patents) for CN 106097335 published on Nov. 9, 2016.
Machine Translation (by Google Patents) for CN 106137760 published on Nov. 23, 2016.
Machine Translation (by Google Patents) for CN 106204599 published on Dec. 7, 2016.
Machine Translation (by Google Patents) for CN 106373137 published on Feb. 1, 2017.
Machine Translation (by Google Patents) for CN 106923787 published on Jul. 7, 2017.
Machine Translation (by Google Patents) for CN 106934799 published on Jul. 7, 2017.
Machine Translation (by Google Patents) for CN 107174188 published on Sep. 19, 2017.
Machine Translation (by Google Patents) for CN 107233580 published on Oct. 10, 2017.
Machine Translation (by Google Patents) for CN 107240091 published on Oct. 10, 2017.
Machine Translation (by Google Patents) for CN 107375951 published on Nov. 24, 2017.
Machine Translation (by Google Patents) for CN 1829466 published on Sep. 6, 2006.
Machine Translation (by Google Patents) for CN 202483565 published on Oct. 10, 2012.
Machine Translation (by Google Patents) for CN 202699138 published on Jan. 30, 2013.
Machine Translation (by Google Patents) for CN 202821355 published on Mar. 27, 2013.
Machine Translation (by Google Patents) for CN 202843564 published on Apr. 3, 2013.
Machine Translation (by Google Patents) for CN 202843608 published on Apr. 3, 2013.
Machine Translation (by Google Patents) for CN 202875332 published on Apr. 17, 2013.
Machine Translation (by Google Patents) for CN 203634116 published on Jun. 11, 2014.
Machine Translation (by Google Patents) for CN 205108749 published on Mar. 30, 2016.
Machine Translation (by Google Patents) for CN 205758500 published on Dec. 7, 2016.
Machine Translation (by Google Patents) for CN 205913317 published on Feb. 1, 2017.
Machine Translation (by Google Patents) for CN 205928774 published on Feb. 8, 2017.
Machine Translation (by Google Patents) for JP 2001062397 published on Mar. 13, 2001.
Machine Translation (by Google Patents) for JP 2010503451 published on Feb. 4, 2010.

* cited by examiner

Figure 2

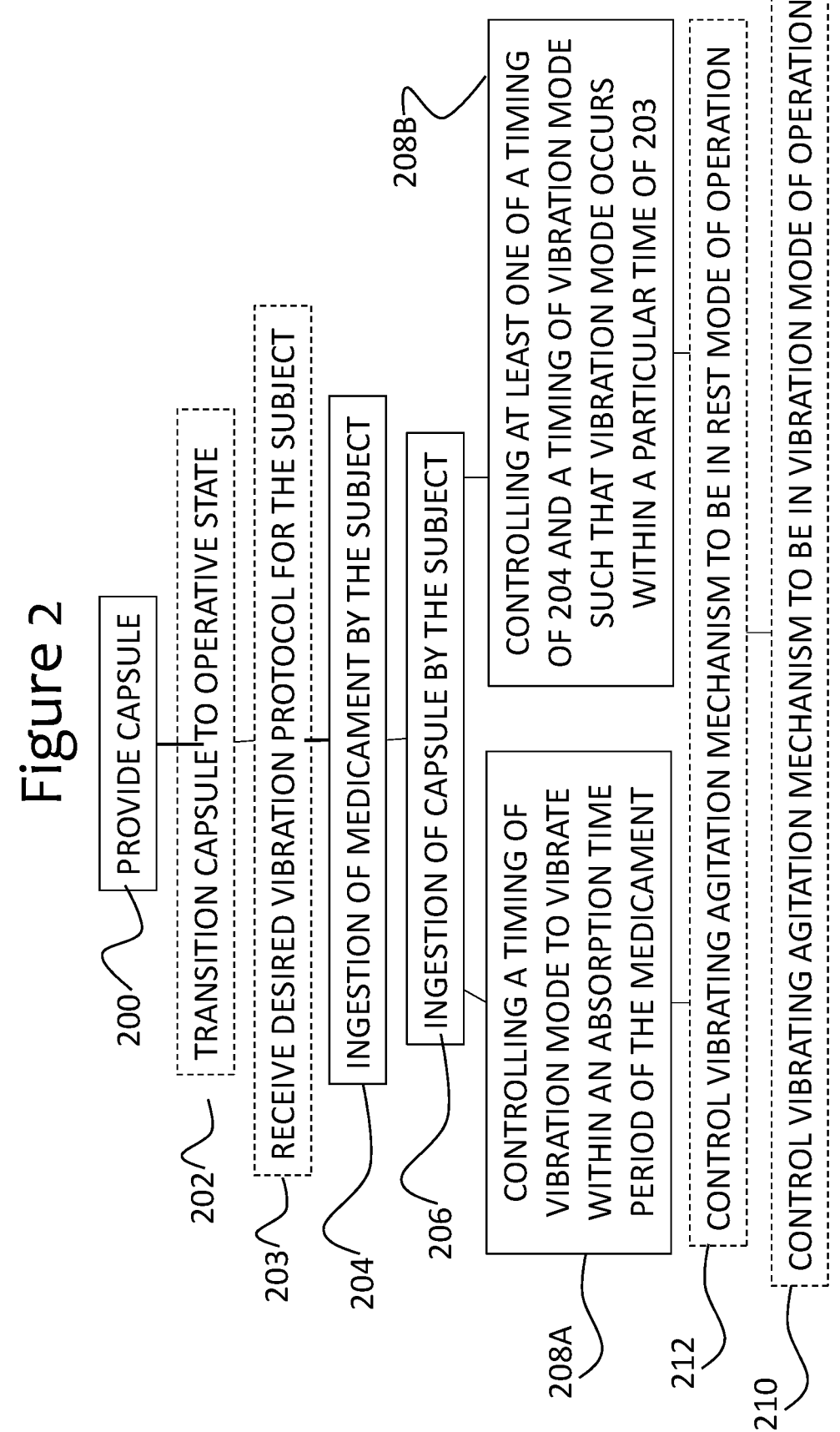

200 PROVIDE CAPSULE

202 TRANSITION CAPSULE TO OPERATIVE STATE

203 RECEIVE DESIRED VIBRATION PROTOCOL FOR THE SUBJECT

204 INGESTION OF MEDICAMENT BY THE SUBJECT

206 INGESTION OF CAPSULE BY THE SUBJECT

208B CONTROLLING AT LEAST ONE OF A TIMING OF 204 AND A TIMING OF VIBRATION MODE SUCH THAT VIBRATION MODE OCCURS WITHIN A PARTICULAR TIME OF 203

208A CONTROLLING A TIMING OF VIBRATION MODE TO VIBRATE WITHIN AN ABSORPTION TIME PERIOD OF THE MEDICAMENT

212 CONTROL VIBRATING AGITATION MECHANISM TO BE IN REST MODE OF OPERATION

210 CONTROL VIBRATING AGITATION MECHANISM TO BE IN VIBRATION MODE OF OPERATION

VIBRATING CAPSULE FOR ENHANCING ABSORPTION OF INGESTED MEDICAMENTS

FIELD OF THE INVENTION

The present invention relates in general to vibrating capsules or vibrating capsule systems including one or more vibrating capsules, and to treatment methods using such systems and capsules, and more particularly, to vibrating capsules and vibrating capsules systems and methods for enhancing the absorption to the bloodstream of an ingested medicament.

SUMMARY OF THE INVENTION

In accordance with an embodiment of the present invention, there is provided a vibrating ingestible capsule for promoting absorption of an ingested medicament into the blood stream, the vibrating ingestible capsule including:

a housing;

a vibrating agitation mechanism adapted such that, in a vibration mode of operation, the housing exerts vibrations on an environment surrounding the vibrating gastrointestinal capsule;

a power supply disposed within the housing and adapted to power the vibrating agitation mechanism; and a control mechanism adapted to activate the vibrating agitation mechanism to be operative in the vibration mode of operation, the control mechanism adapted to control a timing or activation delay of the vibration mode of operation such that a first occurrence of the vibration mode of operation at least partially transpires within at least one of an estimated absorption time period and an actual absorption time period of the ingested medicament within the gastrointestinal tract of the subject.

In some embodiments, the vibrating ingestible capsule is devoid of a chamber for containing the ingested medicament, prior to ingestion thereof.

In some embodiments, operation of the vibrating agitation mechanism in the vibration mode of operation maintains the integrity of the housing.

In some embodiments, operation of the vibrating agitation mechanism in the vibration mode of operation maintains the integrity of the vibrating ingestible capsule.

In some embodiments, the control mechanism is further adapted to control a timing of the vibration mode of operation such that a second occurrence of the vibration mode of operation transpires while the capsule is within at least one of the large intestine and the colon of the subject.

In some such embodiments, the control mechanism is further adapted to control a timing of the vibration mode of operation such that between the first and the second occurrences of the vibration mode of operation, the vibration agitation mechanism is in a rest mode of operation.

In some embodiments, the control mechanism is adapted to activate the vibration agitation mechanism to be operative in the vibration mode of operation in response to receipt of an activation input.

In some embodiments, the vibrating ingestible capsule further includes at least one sensor adapted to provide the activation input.

In some embodiments, the at least one sensor includes an illumination sensor, and the receiving the at least one activation input includes receiving input indicating transition of the capsule from an illuminated environment to a dark environment.

In some embodiments, the at least one sensor includes a pressure sensor and the receiving the at least one activation input includes receiving input indicting pressure applied to the capsule, which pressure is indicative of the capsule moving through a pharynx of the subject.

In some embodiments, the at least one sensor includes a temperature sensor, and the receiving the at least one activation input includes receiving input indicating transition of the capsule from an area with ambient temperature to an area with a human body temperature.

In some embodiments, the at least one sensor includes an accelerometer, and the receiving the at least one activation input includes receiving the activation input in response to a detected activation motion carried out with the gastrointestinal capsule.

In some embodiments, the at least one sensor includes a moisture sensor, and the receiving the at least one activation input includes receiving input indicating transition of the capsule from a dry environment to a humid environment.

In some embodiments, the vibrating ingestible capsule is functionally associated with a control unit remote from the vibrating ingestible capsule, and the control mechanism is adapted to receive the activation input from the control unit.

In some embodiments, the control mechanism is adapted to receive the activation input following ingesting of the vibrating capsule.

In some embodiments, the control mechanism is adapted to receive the activation input prior to ingesting of the vibrating capsule.

In some embodiments, the control mechanism is adapted to receive the activation input by receiving a vibration protocol to be used by the control mechanism to control operation of the vibrating agitation mechanism.

In some embodiments, the vibrating agitation mechanism includes at least a radial agitation mechanism adapted, in the vibration mode of operation, to exert radial forces on the housing, in a radial direction with respect to a longitudinal axis of the housing, thereby to cause the vibrations exerted by the housing.

In some embodiments, the vibrating agitation mechanism includes at least an axial agitation mechanism adapted, in the vibration mode of operation, to exert axial forces on the housing, in an axial direction with respect to a longitudinal axis of the housing, thereby to cause the vibrations exerted by the housing.

In some embodiments, the vibrating agitation mechanism includes a radial agitation mechanism adapted to exert the radial forces and a separate axial agitation mechanism adapted to exert the axial forces.

In some embodiments, the vibrating agitation mechanism includes a single agitation mechanism adapted to exert the radial forces and the axial forces.

In some embodiments, the control mechanism is adapted to control the vibrating agitation mechanism such that the vibrating mode of operation includes a plurality of cycles, each of the cycles including a vibration duration followed by a repose duration, wherein the housing exerts the vibrations during the vibration duration.

In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, 4 seconds to 6 seconds, or 5 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, a duration of each of the plurality of cycles is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, the control mechanism is adapted to control the vibrating agitation mechanism such that a cumulative duration of the vibrating mode of operation is in the range of 1 hour to 12 hours, 2 hours to 10 hours, 2 hours to 8 hours, 2 hours to 6 hours, 2 hours to 4 hours, or 2 hours to 3 hours.

In some embodiments, in the first vibration mode of operation, the vibrating agitation mechanism is configured such that a net force exerted by the housing on the environment is in the range of 50 grams-force to 600 grams-force.

In some embodiments, in the first vibration mode of operation the vibrating agitation mechanism is configured to exert the forces on the housing to attain a vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

In accordance with another embodiment of the present invention, there is provided a method of using a vibrating gastrointestinal capsule in coordination with an ingestible medicament, the method including:

(a) providing the vibrating gastrointestinal capsule, the capsule including:

a housing;

a vibrating agitation mechanism adapted such that, in a vibration mode of operation, the housing exerts vibrations on an environment surrounding the vibrating gastrointestinal capsule;

a power supply disposed within the housing and adapted to power the vibrating agitation mechanism; and a control mechanism adapted to activate the vibrating agitation mechanism to operate in the vibration mode of operation;

(b) ingesting the ingestible medicament;

(c) ingesting the vibrating gastrointestinal capsule; and (d) controlling at least one of a time of the ingesting of the vibrating gastrointestinal capsule and a timing or activation delay of the vibration mode of operation, such that a first occurrence of the vibration mode of operation at least partially transpires within at least one of an estimated absorption time period and an actual absorption time period of the ingestible medicament within the gastrointestinal tract of the subject.

In some embodiments, the controlling comprises controlling the operation of the vibrating agitation mechanism in the vibration mode of operation to maintain the integrity of the housing.

In some embodiments, the controlling comprises controlling the operation of the vibrating agitation mechanism in the vibration mode of operation to maintain the integrity of the vibrating ingestible capsule.

In some embodiments, the controlling further includes controlling a timing of the vibration mode of operation such that a second occurrence of the vibration mode of operation transpires while the capsule is within at least one of the large intestine and the colon of the subject.

In some embodiments, the controlling further includes controlling a timing of the vibration mode of operation such that between the first and the second occurrences of the vibration mode of operation, the vibration agitation mechanism is in a rest mode of operation.

In some embodiments, the controlling is effected such that the vibration mode of operation at least partially transpires during the actual absorption time.

In some embodiments, the actual absorption time period occurs when the ingestible medicament is disposed in a stomach of the subject. In some embodiments, the actual absorption time period occurs when the ingestible medicament is disposed in a small intestine of the subject. In some embodiments, the actual absorption time period occurs when the ingestible medicament is disposed in a large intestine of the subject.

In some embodiments, the controlling of is effected such that the vibration mode of operation at least partially transpires during the estimated absorption time. In some embodiments, the estimated absorption time is within a range of 0.5 to 1.5 hours. In some embodiments, the estimated absorption time is within a range of 1.0 to 5 hours. In some embodiments, the estimated absorption time is within a range of 0.5 to 5 hours. In some embodiments, the estimated absorption time is within a range of 4 to 30 hours.

In some embodiments, the ingesting of the vibrating gastrointestinal capsule transpires within 4 hours, within 3.5 hours, within 3 hours, within 2.5 hours, within 2 hours, within 1.5 hours, within 1 hour, or within 0.5 hours of, or after, the ingesting of the ingestible medicament.

In some embodiments, the ingesting of the vibrating gastrointestinal capsule is simultaneous with the ingesting of the ingestible medicament.

In some embodiments, the method further includes timing the vibration mode of operation to at least partially transpire within 5 hours, within 4 hours, within 3.5 hours, within 3 hours, within 2.5 hours, within 2 hours, within 1.5 hours, within 1 hour, or within 0.5 hours of the ingesting of the ingestible medicament.

In some embodiments, the ingestible medicament is at least partially absorbable in a stomach of a subject or in the stomach of the subject. In some embodiments, the ingestible medicament is at least partially absorbable in a small intestine of a subject or in the small intestine of the subject.

In some embodiments, the ingestible medicament includes an ingestible medicament for treatment of Parkinsonism. In some embodiments, the ingestible medicament for treatment of Parkinsonism includes levodopa. In some embodiments, the ingestible medicament for treatment of Parkinsonism includes at least one dopaminergic agent. In some embodiments, the ingestible medicament for treatment of Parkinsonism includes at least one catecholamine precursor. In some embodiments, the at least one catecholamine precursor includes a dopamine precursor. In some such embodiments, the dopamine precursor includes at least one dopamine precursor agent such as (L)-3,4-dihydroxyphenyl-alanine. In some embodiments, the ingestible medicament for treatment of Parkinsonism includes N-methyl-N-(2-pro-pynyl)-2-methyl-1-phenylethyl-2-amine. In some embodi-ments, the ingestible medicament for treatment of Parkin-sonism includes tyrosine hydroxylase. In some embodiments, the ingestible medicament for treatment of Parkinsonism includes apomorphine. In some embodiments, the ingestible medicament for treatment of Parkinsonism includes at least one anticholinergic agent. In some embodi-ments, the ingestible medicament for treatment of Parkin-sonism includes at least one agent selected to antagonize at least one cholinergic receptor. In some embodiments, the ingestible medicament for treatment of Parkinsonism includes at least one of benzhexol and orphenadrine. In some embodiments, the ingestible medicament for treatment of Parkinsonism includes at least one selective allosteric poten-tiator of metabotropic glutamate receptor 4 (mGluR4), optionally N-phenyl-7-(hydroxylimino)cyclopropa[b] chromen-1a-carboxamide.

In some embodiments, the ingestible medicament for treatment of Parkinsonism is adapted to delay an onset of Parkinsonism. In some embodiments, the ingestible medi-cament for treatment of Parkinsonism is adapted to mitigate or retard a development of Parkinsonism. In some embodi-ments, the ingestible medicament for treatment of Parkin-sonism is adapted to manage a condition of Parkinsonism.

In some embodiments, the ingestible medicament includes an ingestible medicament for treatment of an ail-ment of the GI tract.

In some embodiments, the ingestible medicament for treatment of an ailment of the GI tract includes an ingestible medicament for treatment of constipation. In some embodi-ments, the ingestible medicament for treatment of an ailment of the GI tract includes an ingestible medicament for treat-ment of Crohn's disease. In some embodiments, the ingest-ible medicament for treatment of an ailment of the GI tract includes an ingestible medicament for treatment of gastro-paresis. In some embodiments, the ingestible medicament for treatment of an ailment of the GI tract includes an ingestible medicament for treatment of irritable bowel syn-drome (IBS). In some embodiments, the ingestible medica-ment for treatment of an ailment of the GI tract includes an ingestible medicament for treatment of diarrhea or loose bowel movements. In some embodiments, the ingestible medicament for treatment of an ailment of the GI tract includes an ingestible medicament for treatment of colitis. In some embodiments, the ingestible medicament for treatment of an ailment of the GI tract includes an ingestible medica-ment for treatment of Hirschsprung's disease. In some embodiments, the ingestible medicament for treatment of an ailment of the GI tract includes an ingestible medicament for treatment of dyspepsia. In some embodiments, the ingestible medicament for treatment of an ailment of the GI tract includes an ingestible medicament for treatment of dyspha-gia.

In some embodiments, the ingestible medicament for treatment of an ailment of the GI tract includes at least one osmotic agent, such as magnesium citrate, magnesium hydroxide, polyethylene glycol, or sodium phosphate. In some embodiments, the ingestible medicament for treatment of an ailment of the GI tract includes MiraLAX®. In some embodiments, the ingestible medicament for treatment of an ailment of the GI tract includes at least one contraction stimulating agent, such as bisacodyl or senna. In some embodiments, the ingestible medicament for treatment of an ailment of the GI tract includes at least one of Correctol, Ducodyl, Dulcolax, Senexon, and Senokot. In some embodi-ments, the ingestible medicament for treatment of an ailment of the GI tract includes at least one stool softening agent, such as docusate sodium. In some embodiments, the ingest-ible medicament for treatment of an ailment of the GI tract includes Colace. In some embodiments, the ingestible medi-cament for treatment of an ailment of the GI tract includes linaclotide. In some embodiments, the ingestible medica-ment for treatment of an ailment of the GI tract includes lactulose. In some embodiments, the ingestible medicament for treatment of an ailment of the GI tract includes lubipro-stone. In some embodiments, the ingestible medicament for treatment of an ailment of the GI tract includes plecanatide. In some embodiments, the ingestible medicament for treat-ment of an ailment of the GI tract includes prucaltride. In some embodiments, the ingestible medicament for treatment of an ailment of the GI tract includes a fluid absorption agent, such as loperamide or bismuth subsalicylate.

In some embodiments, the medicament for treatment of an ailment of the GI tract is adapted to reduce constipation. In some embodiments, the medicament for treatment of an ailment of the GI tract is adapted to change the consistency of stool. In some embodiments, the medicament for treat-ment of an ailment of the GI tract is adapted to reduce straining while defecating. In some embodiments, the medi-cament for treatment of an ailment of the GI tract is adapted to reduce a sensation of abdominal bloating. In some embodiments, the medicament for treatment of an ailment of the GI tract is adapted to affect the microbiome of at least a portion of the GI tract. In some embodiments, the medica-ment for treatment of an ailment of the GI tract is adapted to manage a condition of the ailment of the GI tract.

In some embodiments, the vibration mode of operation at least partially transpiring within at least one of an estimated absorption time period and an actual absorption time period of the ingestible medicament within the gastrointestinal tract of the subject the effects an increased absorption of the ingestible medicament, thereby improving a therapeutic efficacy of the medicament.

In some embodiments, the vibration mode of operation at least partially transpiring within at least one of an estimated absorption time period and an actual absorption time period of the ingestible medicament within the gastrointestinal tract of the subject effects an increased absorption of the ingest-ible medicament, thereby enabling the use of a lower dosage of the medicament, optionally without impairing or dimin-ishing therapeutic efficacy.

In some embodiments, the vibration mode of operation is effected within the gastrointestinal tract so as to stimulate the enteric nervous system of the subject. In some embodiments, the vibration mode of operation is effected within the gastrointestinal tract so as to induce at least one peristaltic wave in a wall of the gastrointestinal tract. In some embodi-ments, the vibration mode of operation is effected within the gastrointestinal tract so as to effect increasing peristalsis in a wall of the gastrointestinal tract. In some embodiments, increasing peristalsis is effected so as to stimulate the enteric nervous system of the subject.

In some embodiments, the vibrating gastrointestinal cap-sule is adapted and/or dimensioned to transit the gastroin-testinal tract of the subject or of a subject.

In some embodiments, the capsule further includes a control mechanism adapted, in response to receipt of an activation input, to activate the vibrating agitation mecha-nism to operate in the vibration mode of operation.

In some embodiments, the capsule further includes at least one sensor adapted to provide the activation input.

In some embodiments, the at least one sensor includes an illumination sensor, and the receiving the at least one activation input includes receiving input indicating transition of the capsule from an illuminated environment to a dark environment.

In some embodiments, the at least one sensor includes a pressure sensor and the receiving the at least one activation input includes receiving input indicting pressure applied to the capsule, which pressure is indicative of the capsule moving through a pharynx of the subject.

In some embodiments, the at least one sensor includes a temperature sensor, and the receiving the at least one activation input includes receiving input indicating transition of the capsule from an area with ambient temperature to an area with a human body temperature.

In some embodiments, the at least one sensor includes an accelerometer, and the receiving the at least one activation input includes receiving the activation input in response to a detected activation motion carried out with the gastrointestinal capsule.

In some embodiments, the at least one sensor includes a moisture sensor, and the receiving the at least one activation input includes receiving input indicating transition of the capsule from a dry environment to a humid environment.

In some embodiments, the receipt of the activation input includes receiving the activation input from a control unit remote from the gastrointestinal capsule. In some embodiments, receiving the activation input includes receiving the activation input following the ingesting. In some embodiments, receiving the activation input includes receiving the activation input prior to the ingesting. In some embodiments, receiving the activation input additionally includes receiving a vibration protocol to be used by the control mechanism to control operation of the vibrating agitation mechanism.

In some embodiments, the vibrating agitation mechanism includes at least a radial agitation mechanism, and the controlling includes controlling the radial agitation mechanism, in the vibration mode of operation, to exert radial forces on the housing, in a radial direction with respect to a or the longitudinal axis of the housing, thereby to cause the vibrations exerted by the housing.

In some embodiments, the vibrating agitation mechanism includes at least an axial agitation mechanism, and wherein the control mechanism is adapted to control the axial agitation mechanism, in the vibration mode of operation, to exert axial forces on the housing, in an axial direction with respect to a or the longitudinal axis of the housing, thereby to cause the vibrations exerted by the housing.

In some embodiments, the control mechanism is adapted to control the vibrating agitation mechanism, in the vibration mode of operation, to exert radial forces on the housing in a radial direction with respect to a or the longitudinal axis of the housing and to exert axial forces on the housing in an axial direction with respect to a or the longitudinal axis of the housing, thereby to cause the vibrations exerted by the housing.

In some embodiments, the vibrating agitation mechanism includes a radial agitation mechanism adapted to exert the radial forces and a separate axial agitation mechanism adapted to exert the axial forces.

In some embodiments, the vibrating agitation mechanism includes a single agitation mechanism adapted to exert the radial forces and the axial forces.

In some embodiments, the control mechanism is adapted to control the vibrating agitation mechanism such that the vibrating mode of operation includes a plurality of cycles, each of the cycles including a vibration duration followed by a repose duration, wherein the housing exerts the vibrations during the vibration duration.

In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, 4 seconds to 6 seconds, or 5 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, a duration of each of the plurality of cycles is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, the control mechanism is adapted to control the vibrating agitation mechanism such that a cumulative duration of the vibrating mode of operation is in the range of 1 hour to 12 hours, 2 hours to 10 hours, 2 hours to 8 hours, 2 hours to 6 hours, 2 hours to 4 hours, or 2 hours to 3 hours.

In some embodiments, in the first vibration mode of operation, the vibrating agitation mechanism is configured such that a net force exerted by the housing on the environment is in the range of 50 grams-force to 600 grams-force.

In some embodiments, in the first vibration mode of operation the vibrating agitation mechanism is configured to exert the forces on the housing to attain a vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

In accordance with a further embodiment of the present invention, there is provided a method of using a vibrating gastrointestinal capsule in coordination with an ingestible medicament, the method including:

(a) providing the vibrating gastrointestinal capsule, the capsule including:
    a housing;
    a vibrating agitation mechanism adapted such that, in a vibration mode of operation, the housing exerts vibrations on an environment surrounding the vibrating gastrointestinal capsule;
    a power supply disposed within the housing and adapted to power the vibrating agitation mechanism; and
    a control mechanism adapted to activate the vibrating agitation mechanism to operate in the vibration mode of operation;
  (b) ingesting the vibrating gastrointestinal capsule;

(c) ingesting the ingestible medicament; and (d) controlling at least one of a time of ingesting the vibrating gastrointestinal capsule and a timing of the vibration mode of operation such that a first occurrence of the vibration mode at least partially transpires within a particular time period with respect to the ingesting of the ingestible medicament.

In some embodiments, the controlling comprises controlling the operation of the vibrating agitation mechanism in the vibration mode of operation to maintain the integrity of the housing.

In some embodiments, the controlling comprises controlling the operation of the vibrating agitation mechanism in the vibration mode of operation to maintain the integrity of the vibrating ingestible capsule.

In some embodiments, the controlling further includes controlling a timing of the vibration mode of operation such that a second occurrence of the vibration mode of operation transpires while the capsule is within at least one of the large intestine and the colon of the subject.

In some embodiments, the controlling further includes controlling a timing of the vibration mode of operation such that between the first and the second occurrences of the vibration mode of operation, the vibration agitation mechanism is in a rest mode of operation.

In some embodiments, the particular time period is within 5 hours, within 4 hours, within 3.5 hours, within 3 hours, within 2.5 hours, within 2 hours, within 1.5 hours, within 1 hour, or within 0.5 hours of the ingesting of the ingestible medicament.

In some embodiments, controlling includes both controlling the time of ingesting the vibrating gastrointestinal capsule and the timing of the vibration mode of operation.

In some embodiments, controlling is effected so as to improve absorption of the ingestible medicament within a gastrointestinal tract of a subject.

In accordance with another embodiment of the present invention, there is provided a method of using a vibrating gastrointestinal capsule in coordination with an ingestible medicament, the method including:

(a) providing the vibrating gastrointestinal capsule, the capsule including:

a housing;

a vibrating agitation mechanism adapted such that, in a vibration mode of operation, the housing exerts vibrations on an environment surrounding the vibrating gastrointestinal capsule;

a power supply disposed within the housing and adapted to power the vibrating agitation mechanism; and a control mechanism adapted to activate the vibrating agitation mechanism to operate in the vibration mode of operation;

(b) ingesting the ingestible medicament;

(c) ingesting the vibrating gastrointestinal capsule; and (d) controlling at least one of a time of the ingesting of the vibrating gastrointestinal capsule and a timing or activation delay of the vibration mode of operation, such that a first occurrence of the vibration mode of operation at least partially transpires within an estimated absorption time period of the ingestible medicament within the gastrointestinal tract of the subject.

In some embodiments, the controlling comprises controlling the operation of the vibrating agitation mechanism in the vibration mode of operation to maintain the integrity of the housing.

In some embodiments, the controlling comprises controlling the operation of the vibrating agitation mechanism in the vibration mode of operation to maintain the integrity of the vibrating ingestible capsule.

In some embodiments, the controlling further includes controlling a timing of the vibration mode of operation such that a second occurrence of the vibration mode of operation transpires while the capsule is within at least one of the large intestine and the colon of the subject.

In some embodiments, the controlling further includes controlling a timing of the vibration mode of operation such that between the first and the second occurrences of the vibration mode of operation, the vibration agitation mechanism is in a rest mode of operation.

In accordance with a further embodiment of the present invention, there is provided a method of using a vibrating gastrointestinal capsule in coordination with an ingestible medicament, the method including:

(a) providing the vibrating gastrointestinal capsule, the capsule including:

a housing;

a vibrating agitation mechanism adapted such that, in a vibration mode of operation, the housing exerts vibrations on an environment surrounding the vibrating gastrointestinal capsule;

a power supply disposed within the housing and adapted to power the vibrating agitation mechanism; and a control mechanism adapted to activate the vibrating agitation mechanism to operate in the vibration mode of operation;

(b) ingesting the ingestible medicament;

(c) ingesting the vibrating gastrointestinal capsule; and (d) controlling at least one of a time of the ingesting of the vibrating gastrointestinal capsule and a timing or activation delay of the vibration mode of operation, such that a first occurrence of the vibration mode of operation at least partially transpires within an actual absorption time period of the ingestible medicament within the gastrointestinal tract of the subject.

In some embodiments, the controlling comprises controlling the operation of the vibrating agitation mechanism in the vibration mode of operation to maintain the integrity of the housing.

In some embodiments, the controlling comprises controlling the operation of the vibrating agitation mechanism in the vibration mode of operation to maintain the integrity of the vibrating ingestible capsule.

In some embodiments, the controlling further includes controlling a timing of the vibration mode of operation such that a second occurrence of the vibration mode of operation transpires while the capsule is within at least one of the large intestine and the colon of the subject.

In some embodiments, the controlling further includes controlling a timing of the vibration mode of operation such that between the first and the second occurrences of the vibration mode of operation, the vibration agitation mechanism is in a rest mode of operation.

In accordance with yet another embodiment of the present invention, there is provided a kit for promoting absorption of an ingested medicament into the blood stream, the kit including:

a medicament to be ingested; and vibrating ingestible capsule including:

a vibrating agitation mechanism adapted such that, in a vibration mode of operation, the housing exerts vibrations on an environment surrounding the vibrat-
ing gastrointestinal capsule;

a power supply disposed within the housing and
adapted to power the vibrating agitation mechanism;
and a control mechanism adapted to activate the vibrating
agitation mechanism to operative in the vibration
mode of operation, the control mechanism adapted to
control a timing or activation delay of the vibration
mode of operation such that a first occurrence of the
vibration mode of operation at least partially tran-
spires within at least one of an estimated absorption
time period and an actual absorption time period of
the ingested medicament within the gastrointestinal
tract of the subject.

In some embodiments, the vibrating ingestible capsule is
devoid of a chamber for containing the medicament to be
ingested.

In accordance with a further embodiment of the present
invention, there is provided use of a vibrating ingestible
capsule for promoting absorption of an ingested medicament
into the blood stream, the vibrating ingestible capsule
including:

a housing;

a vibrating agitation mechanism adapted such that, in a
vibration mode of operation, the housing exerts vibra-
tions on an environment surrounding the vibrating
gastrointestinal capsule;

a power supply disposed within the housing and adapted
to power the vibrating agitation mechanism; and a control mechanism adapted to activate the vibrating
agitation mechanism to operative in the vibration mode
of operation, the control mechanism adapted to control
a timing or activation delay of the vibration mode of
operation such that a first occurrence of the vibration
mode of operation at least partially transpires within at
least one of an estimated absorption time period and an
actual absorption time period of the ingested medica-
ment within the gastrointestinal tract of the subject.

BRIEF DESCRIPTION OF THE FIGURES

The foregoing discussion will be understood more readily
from the following detailed description of the invention,
when taken in conjunction with the accompanying FIGS.
1-2), in which:

FIG. 2 is a schematic flowchart of a method for using a
vibrating gastrointestinal capsule to improve or accelerate
the absorption to the bloodstream of an ingestible medica-
ment, or to improve the efficacy of such a medicament,
according to the present invention, the method being based
on use of an ingestible vibrating gastrointestinal capsule, for
example as shown in FIG. 1.

DESCRIPTION OF THE PREFERRED EMBODIMENTS

Figure 1:
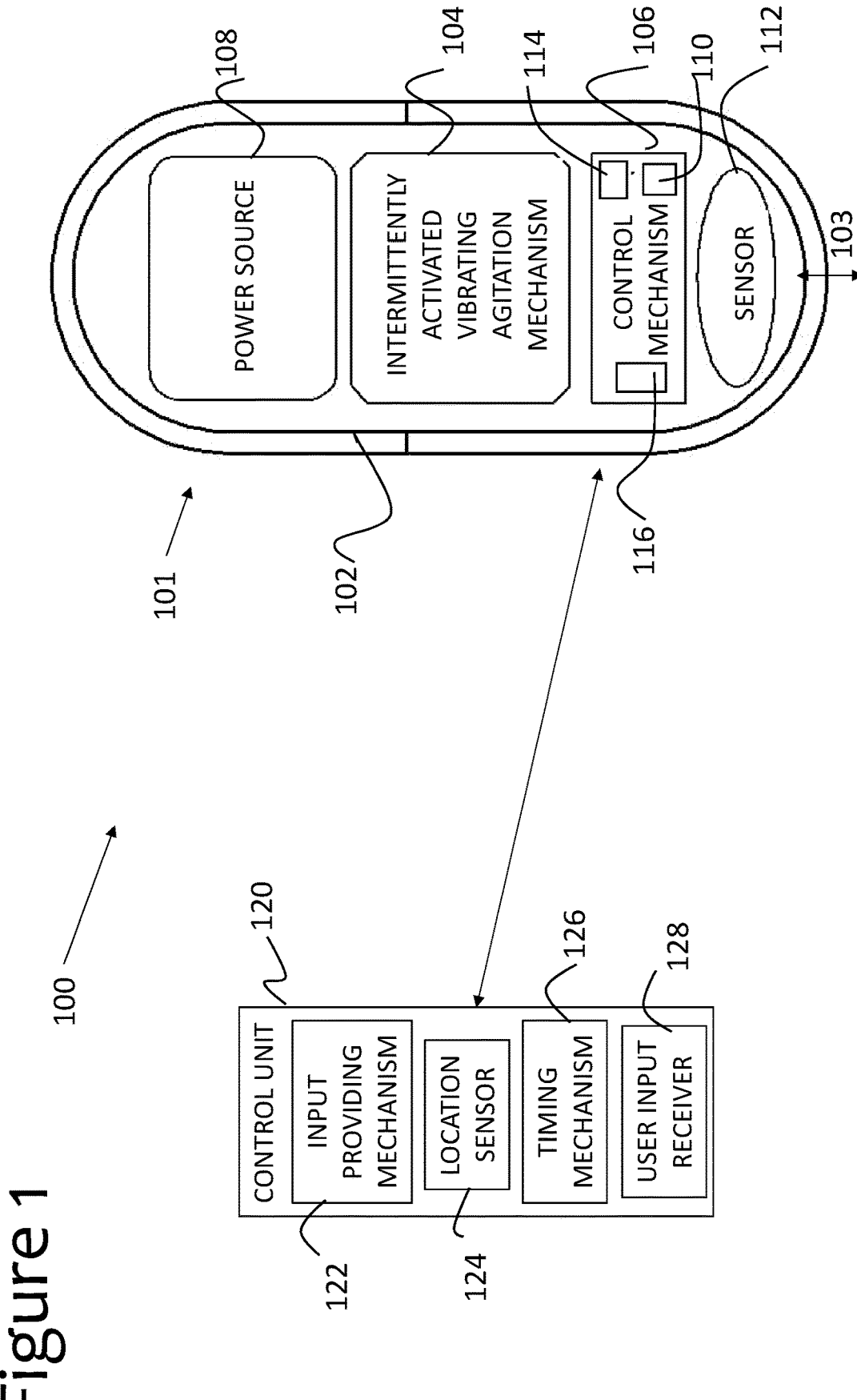
FIG. 1 is a schematic block diagram of a gastrointestinal
treatment system including a vibrating ingestible capsule
according to an embodiment of the present invention.

The principles of the inventive gastrointestinal treatment
system and method of enhancing the absorption into the
bloodstream of ingestible medicaments, for example ingest-
ible medicaments for treating Parkinsonism or for treating
an ailment of the gastrointestinal (GI) tract, using the inventive gastrointestinal treatment system, may be better
understood with reference to the drawings and the accom-
panying description.

Before explaining at least one embodiment of the inven-
tion in detail, it is to be understood that the invention is not
limited in its application to the details of construction and
the arrangement of the components set forth in the following
description or illustrated in the drawings. The invention is
capable of other embodiments or of being practiced or
carried out in various ways. Also, it is to be understood that
the phraseology and terminology employed herein is for the
purpose of description and should not be regarded as lim-
iting.

For the purposes of this application, the term "subject"
relates to a human.

For the purposes of this application, the term "vibrating
ingestible capsule" relates to an ingestible capsule adapted
to at least intermittently vibrate, for a cumulative duration of
at least one minute, in accordance with a vibration protocol
of the capsule.

For the purposes of this application, the term "vibrating
agitation mechanism" refers to any type of mechanism that
vibrates or causes elements in its vicinity to vibrate, includ-
ing a vibration motor or engine and a pendulum.

For the purposes of this application, the term "intermit-
tently activated vibrating agitation mechanism" refers to a
vibration agitation mechanism that vibrates or causes ele-
ments in its vicinity to vibrate and is operative at certain
times, and does not vibrate or cause elements in its vicinity
to vibrate at other times, the activation times being selected
by a control mechanism or other control unit controlling the
vibration agitation mechanism.

For the purposes of this application, the term "vibration
protocol" relates to a protocol specifying vibration param-
eters of an intermittently activated vibrating agitation
mechanism of a vibrating ingestible capsule. Typically, the
vibration protocol relates to an activation delay for initiating
vibration (e.g., a duration between "initial" activation of the
capsule and the first activation of the vibration agitation
mechanism), a vibration rate (number of vibration cycles per
hour), a vibration duration and a repose duration for each
vibration cycle, a vibration frequency, an amount of force
exerted by the vibrations, and the like.

For the purposes of this application, the term "treatment
procedure" relates to parameters of a treatment utilizing
vibrating ingestible capsules, which are typically defined by
a treating physician or medical practitioner. For example, the
treatment procedure may include the number of capsules to
be taken within a specific time duration (e.g., 3 capsules per
week, 2 capsules per day), the frequency at which capsules
should be taken, the time of day at which capsules should be
taken, whether the capsule should be taken with or without
food, and the like.

For the purpose of this application, the term "treatment
protocol" relates to all aspects of treatment of a subject with
a vibrating ingestible capsule, and includes the treatment
procedure as well as the vibration protocol to be used for
treating the subject.

For the purpose of this application, the term "activation
input" relates to an input received by a control mechanism
or control mechanism of a vibrating ingestible capsule,
which causes the control mechanism or control mechanism
of the capsule to activate itself, so as to be able to process
inputs and/or to control additional components of the cap-
sule. The activation input may be received from an element
forming part of the capsule, such as a sensor sensing specific
conditions in which the capsule should be activated, or from a remote source, such as a remote control mechanism, for example by way of a signal transmitted to the capsule, magnetic field applied to the capsule, specific motion applied to the capsule, or any other type of input provided to the capsule from a remote source.

For the purpose of this application, a vibrating ingestible capsule is said to be in an "inoperative state" when the capsule is in a storage condition, intended to preserve the life of a battery thereof. In the inoperative state, components of the capsule which are intended to receive or to provide an activation input, such as specific sensors, transceivers, and/or timing mechanisms may be active at least to a minimal degree. However, in the inoperative state, no vibration takes place, and a control mechanism controlling vibration of the capsule is inactive.

For the purpose of this application, a vibrating ingestible capsule is said to be in an "operative state" when the control mechanism of the capsule is processing inputs and data, and can cause a vibrating agitation mechanism of the capsule to vibrate or cause elements in its vicinity to vibrate.

For the purposes of this application, an action carried out on or in an object is considered to be "maintaining the integrity" of the object, if, during the action and for a duration of at least 24 hours following the action there is no permanent change to the structure of the object, or of any portion of the object, other than movement of movable portions within the object. Specifically, vibration of a vibrating ingestible capsule is considered to maintain the integrity of the vibrating ingestible capsule if, during and following such vibration, there is no permanent change to the mechanical structure of the capsule, such as to the housing thereof, with the exception of movement of the vibrating agitation mechanism or a portion thereof within the capsule.

A test for determining whether or not vibration of a vibrating ingestible capsule is considered to maintain the integrity of the vibrating ingestible capsule or of a housing thereof includes placing the vibrating ingestible capsule in a 250 ml cup of water, where the water is maintained at a human body temperature—i.e. in the range of 36° C. to 37.5° C. The vibration of the capsule is activated, and is allowed to continue for a duration of 30 hours, or until the power source is depleted, in which case the capsule remains in the water following depletion of the power source till the duration of 30 hours is completed. If the mechanical structure of the housing or of capsule is in no way damaged or changed at the end of the 30 hours, the vibration of the capsule maintains the integrity of the housing or of the capsule, respectively.

For the purpose of this application, an "ingestible medicament" is at least partially absorbable to the bloodstream from within the stomach, small intestine, and large intestine, and more typically, within the stomach or small intestine.

For the purpose of this application, the term "partially absorbable" is meant to include the possibility that the environment within the gastrointestinal tract (including acids, enzymes, etc. thereof) may chemically modify the ingested medicament in order to achieve the characteristic "partially absorbable".

For the purpose of this application, an estimated absorption time of an ingestible medicament which is exposed to fluids in the GI tract, may be determined as follows:

(i) ingestible medicaments that are absorbed in the stomach have an estimated absorption time within a range of 0.5 to 1.5 hours from the time of ingestion of the medicament;

(ii) ingestible medicaments that are absorbed in the small intestine have an estimated absorption time within a range of 1.0 to 5 hours from the time of ingestion of the medicament;

(iii) ingestible medicaments that are absorbed in both the stomach and the small intestine have an estimated absorption time within a range of 0.5 to 5 hours from the time of ingestion of the medicament;

(iv) ingestible medicaments that are absorbed in the large intestine have an estimated absorption time of at least 4 hours, and more typically, within a range of 4 to 30 hours, 6 to 30 hours, 6 to 20 hours, or 8 to 20 hours from the time of ingestion of the medicament.

For the purpose of this application, an estimated absorption time of an ingestible medicament which is delivered into the GI tract in a container and is unexposed to the GI tract, may be within a range of 15 minutes to 2 hour from the release of the ingestible medicament into the GI tract and/or from exposure of the ingestible medicament to fluids in the GI tract.

The location within the GI tract at which the particular ingestible medicament is absorbed to the bloodstream may often be public knowledge. This location may be provided by, or known to, the manufacturer and/or distributor of the particular ingestible medicament. Alternatively or additionally, the location may be known to relevant medical practitioners, including doctors and pharmacists, and more particularly, to a medical practitioner of the subject.

For the purpose of this application, an actual absorption time may be determined from clinical data, in vivo or in vitro, according to accepted clinical procedures known to those of skill in the art. Since actual absorption is achieved over a period of time, the "actual absorption time" or "actual absorption time period" may be defined by the time period at which between 20% and 80% of the absorption occurs. In the absence of such data, the "actual absorption time" or "actual absorption time period" may be defined by determining the "peak" actual absorption time, and building a time period of up to 1 hour on each side of the peak time.

For the purpose of this application, the term "Parkinsonism" is meant to include Parkinson's disease, or symptoms of neurodegeneration associated therewith.

For the purpose of this application, the term "Parkinsonism" is meant to include progressive supranuclear palsy, or symptoms of neurodegeneration associated therewith.

For the purpose of this application, the term "Parkinsonism" is meant to include corticobasal degeneration, or symptoms of neurodegeneration associated therewith.

For the purpose of this application, the term "Parkinsonism" is meant to include multiple system atrophy, or symptoms of neurodegeneration associated therewith.

For the purpose of this application, the term "Parkinsonism" is meant to include Parkinson-plus syndromes (also known as disorders of multiple system degeneration), or symptoms of neurodegeneration associated therewith.

For the purpose of this application, the term "Parkinsonism" is meant to include any neurodegenerative disease in which the subject exhibits at least one (and typically at least two or three) of the classical features of Parkinson's disease: tremor, postural instability, and akinesia or bradykesia.

For the purpose of this application, the term "Parkinsonism" is meant to include any neurodegenerative disease in which the subject positively responds to a dopaminergic treatment.

For the purpose of this application, the term "Parkinsonism" is meant to include any neurodegenerative disease in which the particular subject positively responds to an anticholinergic treatment.

For the purpose of this application, the term "Parkinsonism" is meant to include any neurodegenerative disease in which a dopaminergic treatment is clinically utilized to treat the sufferers or subjects.

For the purpose of this application, the term "Parkinsonism" is meant to include any neurodegenerative disease in which an anticholinergic treatment is clinically utilized to treat the sufferers or subjects.

For the purpose of this application, the term "Parkinson's disease" (PD) is meant as used by those of skill in the art of neurodegenerative diseases. It is believed that PD is due to the loss of brain cells that produce dopamine. Early signs and symptoms of Parkinson's disease include at least one of tremors (or trembling), slowness of movement, body rigidity and stiffness, and gait problems.

For the purpose of this application, the term "treatment of Parkinsonism" and the like refers to at least one of: (i) delaying onset of Parkinsonism (e.g., PD); (ii) mitigating the development of Parkinsonism (e.g., PD); and (iii) managing a condition of Parkinsonism (e.g., PD).

For the purpose of this application, the term "ailment of the GI tract" is meant to include chronic or acute constipation, or symptoms associated therewith.

For the purpose of this application, the term "ailment of the GI tract" is meant to include gastroparesis, or symptoms associated therewith.

For the purpose of this application, the term "ailment of the GI tract" is meant to include Crohn's disease, or symptoms associated therewith.

For the purpose of this application, the term "ailment of the GI tract" is meant to include chronic or acute diarrhea, or symptoms associated therewith.

For the purpose of this application, the term "ailment of the GI tract" is meant to include colitis, or symptoms associated therewith.

For the purpose of this application, the term "ailment of the GI tract" is meant to include dyspepsia or dysphagia, or symptoms associated therewith.

For the purpose of this application, the term "ailment of the GI tract" is meant to include Hirschsprung's disease, or symptoms associated therewith.

For the purpose of this application, the term "ailment of the GI tract" is meant to include irritable bowel syndrome, or symptoms associated therewith.

For the purpose of this application, the term "ailment of the GI tract" is meant to include any disease in which the subject positively responds to an osmotic gastrointestinal treatment.

For the purpose of this application, the term "ailment of the GI tract" is meant to include any disease in which the particular subject positively responds to a stool softening treatment.

For the purpose of this application, the term "ailment of the GI tract" is meant to include any disease in which the particular subject positively responds to a GI contraction inducing treatment.

For the purpose of this application, the term "ailment of the GI tract" is meant to include any disease in which the subject positively responds to a GI fluid absorption inducing treatment.

For the purpose of this application, the term "managing a condition of", with respect to Parkinsonism and the like and/or with respect to an ailment of the GI tract, is meant to include, inter alia, improving absorption of a medicament, such as a medicament used in the treatment of Parkinsonism (e.g., levodopa) and/or a medicament used for treatment of the GI tract (e.g. Linaclotide, Linzess®), into the bloodstream. Such condition management may be manifested by at least one of (i) improved medicament efficacy due to the increased absorption; and (ii) reduced dosage of the medicament, due to the increased medicament absorption efficacy.

Referring now to the drawings, FIG. 1 is a schematic block diagram of a gastrointestinal treatment system 100 including a vibrating ingestible capsule 101 according to an embodiment of the present invention.

As seen in FIG. 1, gastrointestinal treatment system 100 includes vibrating ingestible capsule 101. Capsule 101 includes a capsule housing or shell 102, arranged along a longitudinal axis 103 and having disposed therein a vibrating agitation mechanism 104. A control mechanism 106, which may for example be, or include, a processor, is adapted to control operation of vibrating agitation mechanism 104, and at least one power source 108 provides power to vibrating agitation mechanism 104 and control mechanism 106.

Power source 108 may be any suitable power source, such as one or more alkaline or silver oxide batteries, primary batteries, rechargeable batteries, capacitors and/or supercapacitors.

Intermittently activated vibrating agitation mechanism 104 is adapted to have a vibration mode of operation (also termed the first mode of operation) and a rest mode of operation (also termed the second mode of operation). In the vibration mode of operation, intermittently activated vibrating agitation mechanism 104 is adapted to exert forces on capsule housing 102, such that capsule housing 102 exerts vibrations on an environment surrounding capsule 101, while maintaining the integrity of the capsule 101 and of the capsule housing 102.

In some embodiments, the capsule is in an inoperative state, until the receipt of an activation input, which causes control mechanism 106 to transition the capsule from the inoperative state to an operative state.

In some embodiments, control mechanism 106 is functionally associated with, or includes, a timing mechanism 110, powered by power source 108 and adapted to track at least one time characteristic, such as a duration that has passed since an activation input was received, or a duration that has passed since the subject ingested capsule 101.

In some embodiments, capsule 101 is devoid of any sensors for sensing an environment thereof. In some such embodiments, control mechanism 106 is adapted, in response to receipt of an activation input, to wait a predetermined delay time, and following the predetermined delay time, to activate vibrating agitation mechanism 104 to operate in said first vibration mode of operation.

In other embodiments, such as the embodiment illustrated in FIG. 1, capsule 101 further includes at least one sensor 112, functionally associated with control mechanism 106. The at least one sensor 112 may be adapted to sense at least one parameter within capsule 101 or in an environment of capsule 101, and may include a temperature sensor, an illumination sensor, a moisture sensor, a pressure sensor, an accelerometer, or any other suitable sensor. In some embodiments, the at least one sensor 112 is adapted to identify a specific condition in capsule 101 or in the vicinity thereof, and to provide an activation input to control mechanism 106 in response to identification of the condition. For example, in some embodiments the condition is indicative of the subject ingesting capsule 101.

For example, in some embodiments sensor 112 may include an illumination sensor, adapted to identify transition of capsule 101 from an illuminated environment (e.g. outside the human body) to a dark environment (e.g. within the human body) and to provide an activation input in response to identification of such a transition.

As another example, in some embodiments, sensor 112 may include a motion or acceleration sensor, such as an accelerometer, adapted to identify an activation motion carried out by a user on capsule 101 and to provide an activation input in response to identification of such a transition. An example of an accelerometer providing an activation input for a gastrointestinal capsule is provided in U.S. patent application Ser. No. 15/168,065, filed on May 29, 2016, which is incorporated by reference for all purposes as if fully set forth herein.

As another example, in some embodiments, sensor 112 may include a pressure sensor adapted identify pressure applied to the capsule 101, which pressure is indicative of the capsule moving through a pharynx of the subject, and to provide an activation input in response to identification of such pressure.

As a further example, in some embodiments, sensor 112 may include a temperature sensor adapted to identify transition of capsule 101 from an area with ambient temperature (e.g. outside the human body) to an area with a human body temperature and to provide an activation input in response to identification of such a transition.

As another example, in some embodiments, sensor 112 may include a motion or acceleration sensor, such as an accelerometer, adapted to identify an activation motion carried out by a user on capsule 101 and to provide an activation input in response to identification of such a transition.

As a further example, in some embodiments, sensor 112 may include a moisture sensor adapted to identify transition of capsule 101 from a dry area (e.g. outside the human body) to a moist area (e.g. within the human body) and to provide an activation input in response to identification of such a transition.

In some embodiments, system 100 further includes a control unit 120, which may be remote from capsule 101, and which is adapted to provide one or more inputs to the capsule. In some such embodiments, capsule 101 further includes a remote input receiving mechanism 116, functionally associated with control mechanism 106, and adapted to receive inputs from an input providing mechanism 122 of control unit 120.

In some embodiments, control unit 120 may further include a timing mechanism 126, adapted to track at least one time characteristic, such as a duration that has passed since a control instruction was provided to capsule 101.

In some embodiments, control unit 120 may further include a user input receiver 128, such as a keyboard, touch screen, or touch pad, adapted to receive input from a user, such as the subject, a medical professional treating the subject, or a caregiver of the subject.

Control unit 120 may be any suitable type of control unit. In some embodiments, control unit may be a suitably configured smart phone or a tablet computer.

In some such embodiments, control unit 120 may provide inputs to capsule 101 by remotely transmitting the inputs from input providing mechanism 122 to remote input receiving mechanism 116, for example using a short range wireless communication method, such as radio frequency (RF) communication or Bluetooth® communication. One example of such a mechanism for providing input to a capsule is described in U.S. patent application Ser. No. 15/132,039 filed Apr. 18, 2016 and entitled "IN VIVO DEVICE AND METHOD OF USING THE SAME", which is incorporated by reference for all purposes as if fully set forth herein.

In some embodiments, control unit 120 is adapted to provide the activation input to control mechanism 106 of capsule 101. In some such embodiments, control unit 120 provides the activation input prior to the subject ingesting capsule 101, whereas in other embodiments control unit 120 provides the activation input following ingestion of capsule 101 by the subject.

Relating to the characteristics of vibrating agitation mechanism 104, the vibrating agitation mechanism may be any suitable mechanism that can be intermittently activated and can apply suitable forces onto capsule housing 102 while maintaining the integrity of the capsule and of the capsule housing.

In some embodiments, intermittently activated vibrating agitation mechanism 104 may include a radial agitation mechanism adapted to exert radial forces on capsule housing 102, in a radial direction with respect to the longitudinal axis of housing 102. For example, the radial agitation mechanism may include an unbalanced weight attached to a shaft of an electric motor powered by said battery, substantially as described in U.S. Pat. No. 9,707,150, which is incorporated by reference for all purposes as if fully set forth herein.

In some embodiments, intermittently activated vibrating agitation mechanism 104 may include an axial agitation mechanism adapted to exert radial forces on the capsule housing 102, in an axial direction with respect to a longitudinal axis of housing 102. For example, the axial agitation mechanism may include an electric motor powered by the battery and an urging mechanism, associated with, and driven by, the electric motor, such that the urging mechanism adapted to exert said axial forces, substantially as described in U.S. Pat. No. 9,707,150. In some embodiments, the urging mechanism adapted to exert the axial forces in opposite directions. In some embodiments, the urging mechanism is adapted to deliver at least a portion of the axial forces in a knocking mode.

In some embodiments, the forces exerted by intermittently activated vibrating agitation mechanism 104 on capsule housing 102 in the vibration mode of operation include radial forces in a radial direction with respect to the longitudinal axis of the housing and axial forces in an axial direction with respect to the longitudinal axis. In some embodiments, a single agitation mechanism exerts both the radial and the axial forces. In other embodiments, the axial forces are exerted by one agitation mechanism, and the radial forces are exerted by another, separate, agitation mechanism, where both agitation mechanisms form part of intermittently activated vibrating agitation mechanism 104.

In some embodiments, the intermittently activated vibrating agitation mechanism 104 may include a magnet mounted onto a rotor adapted to exert a magnetic field as well as radial forces on capsule housing 102. For example, such a magnetic vibration agitation mechanism is described in U.S. patent application Ser. No. 15/058,216 filed on Mar. 2, 2016 and entitled "PHYSIOTHERAPY DEVICE AND METHOD FOR CONTROLLING THE PHYSIOTHERAPY DEVICE", which is incorporated by reference for all purposes as if fully set forth herein.

In some embodiments, housing 102 may include first and second members, and vibrating agitation mechanism 104 may include a mechanism adapted to effect a vibration by moving the first member of the housing in the opposite direction relative to the second member of the housing, substantially as described in U.S. Pat. No. 9,078,799, which is incorporated by reference for all purposes as if fully set forth herein.

In some embodiments, housing 102 may include a vibration agitation mechanism 104 which makes use of a pendulum to cause vibration in the vicinity of the capsule, for example as described in CN Patent Application Number 105997466 filed on Jun. 16, 2016 and entitled "INTELLIGENT VIBRATING ELECTRONIC CAPSULE", which is incorporated by reference for all purposes as if fully set forth herein.

In the vibrating mode of operation, intermittently activated vibrating agitation mechanism 104 is adapted to have a plurality of vibration cycles, where each cycle includes a vibration duration followed by a repose duration. Forces are exerted by the vibrating agitation mechanism 104 on capsule housing 102 only during the vibration duration, and as such capsule housing 102 only exerts forces on an environment thereof during the vibration duration.

In some embodiments, the number of vibration cycles per hour is in the range of 20 to 400, 40 to 400, 60 to 400, 80 to 400, 40 to 380, 60 to 380, 80 to 380, 40 to 360, 60 to 360, 80 to 360, 100 to 360, 100 to 330, 100 to 300, 100 to 280, 100 to 250, 100 to 220, 100 to 200, 120 to 300, 120 to 280, 120 to 250, 120 to 220, 120 to 200, 150 to 300, 150 to 280, 150 to 250, 150 to 220, 150 to 200, 170 to 300, 170 to 250, 170 to 220, or 170 to 200.

In some embodiments, the repose duration is greater than the vibration duration. In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, or 4 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, the total duration of one vibration cycle is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, the cumulative duration of the vibrating mode of operation, or the cumulative duration during which vibration cycles are occurring, is in the range of 1 hour to 12 hours, 2 hours to 10 hours, 2 hours to 8 hours, 2 hours to 6 hours, 2 hours to 4 hours, or 2 hours to 3 hours. It will be appreciated that the cumulative duration of vibration cycles may be dependent on properties of power source 108.

It will be appreciated by persons skilled in the art that the vibration mode of operation may be intermittent, or interrupted, such that vibrating agitation mechanism 104 is operative in the vibration mode for a first duration, for example 30 minutes, then does have any vibration cycles for a second duration, for example 1 hour, and then is operative in the vibration mode and has vibration cycles for a third duration, for example two hours. The cumulative duration relates to the sum of all durations during which vibrating agitation mechanism 104 was operative in the vibration mode and included vibration cycles, including the vibration duration and the repose duration of the vibration cycle.

In some embodiments, vibrating agitation mechanism 104 is configured to exert forces on the capsule housing 102, such that a net force exerted by the capsule housing 102 on the environment thereof is in the range of 50 grams force (go to 600 gf, 50 gf to 550 gf, 100 gf to 550 gf, 100 gf to 500 gf, 150 gf to 500 gf, 200 gf to 500 gf, or 200 gf to 450 gf.

In some embodiments, vibrating agitation mechanism 104 is configured to exert said forces on capsule housing 102 to attain a capsule housing 102 vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

It will be appreciated that the exact specifications of the capsule, such as the specific frequency and force ranges applicable to a specific capsule, are dependent on the specifications of the power source and of the vibrating agitation mechanism.

It will be further appreciated that a specific capsule may be controlled by the control mechanism such that different vibrational frequencies may be attained and/or different net forces may be exerted, by the capsule in different vibration cycles of the capsule. Due to the natural distinction between subjects, use of multiple different parameters in different vibration cycles of a single capsule would allow the capsule to successfully treat multiple subjects, even if the personal optimal treatment for those subjects is not the same, as there is a higher chance that in at least some of the vibration cycles the activation parameters of the capsule would reach, or be close to, the optimal parameters for each specific subject.

Control mechanism 106 is adapted to control the operation of intermittently activated vibrating agitation mechanism 104. Such control may include control of any one or more of the force applied by the vibrating agitation mechanism, the vibrational frequency reached, the times in which vibrating agitation mechanism 104 operates in the vibration mode of operation, the vibration duration of each vibration cycle, the repose duration of each vibration cycle, the vibration cycle duration, and cumulative vibration duration of the vibrating agitation mechanisms.

In some embodiments, control mechanism 106 is adapted to receive information relating to the desired vibration protocol from control unit 120, prior to ingestion of the capsule or to activation thereof, or during the capsule's traversal of the subject's GI tract. For example, the information may be remotely transmitted from control unit 120 to control mechanism 106, for example using a short range wireless communication method. In some embodiments, the information is transmitted as a list of vibration parameters for effecting the vibration protocol. In some embodiments, the information is transmitted as executable code for effecting the first vibration protocol.

In some embodiments, the information includes a desired number of vibration cycles, a desired vibration duration in each vibration cycle, a desired repose duration in each vibration cycle, a desired cumulative vibration duration, and the like.

Control mechanism 106 may be adapted to control vibrating agitation mechanism 104 so that the capsule applies forces to an environment thereof, such that within the gastrointestinal tract, a mechanical stimulation of the wall of the gastrointestinal tract is effected. As explained in further detail hereinbelow, in some embodiments, control mechanism 106 is adapted to control vibrating agitation mechanism 104 so that the capsule applies forces to an environment thereof during at least two distinct time periods. For example, control mechanism 106 may control vibrating agitation mechanism 104 to be in the vibration mode of operation while the capsule is disposed within the stomach of the user, to be in the rest mode of operation while the capsule traverses the small intestine of the user, and to be again in the vibration mode of operation while the capsule is in the large intestine of the user.

Reference is now additionally made to FIG. 2, which is a schematic flowchart of a method for using a vibrating gastrointestinal capsule to improve or accelerate the absorption into the bloodstream of an ingestible medicament, for example an ingestible medicament for treatment of Parkinsonism or of an ailment of the GI tract, and/or to improve the efficacy of such a medicament, according to the present invention. The method may be based on the use of a gastrointestinal capsule system including (or consisting of) a vibrating ingestible capsule, such as capsule 101 of system 100 of FIG. 1.

As seen at step 200, a vibrating gastrointestinal capsule is provided. The vibrating gastrointestinal capsule may have, as described with respect to FIG. 1, a housing; a vibrating agitation mechanism adapted such that, in a first vibrating mode ("vibration mode") of operation, the housing exerts vibrations on an environment surrounding the vibrating gastrointestinal capsule; and a power supply disposed within the housing and adapted to power the vibrating agitation mechanism. Typically, the capsule includes an on-board control mechanism adapted to control or activate the vibrating agitation mechanism. The control mechanism may form a component of such a vibrating agitation mechanism.

At step 204, an ingestible medicament is ingested by the subject.

In some embodiments, the ingestible medicament may be an ingestible medicament for treatment of Parkinsonism, which may be, or include, any one or more of:
- levodopa;
- at least one dopaminergic agent;
- at least one catecholamine precursor;
- a dopamine precursor; at least one dopamine precursor agent, such as (L)-3,4-dihydroxyphenylalanine;
- N-methyl-N-(2-propynyl)-2-methyl-1-phenylethyl-2-amine;
- tyrosine hydroxylase;
- apomorphine;
- at least one anticholinergic agent;
- at least one agent selected to antagonize at least one cholinergic receptor;
- at least one of benzhexol and orphenadrine; and
- at least one selective allosteric potentiator of metabotropic glutamate receptor 4 (mGluR4), such as N-phenyl-7-(hydroxylimino)cyclopropa[b]chromen-1a-carboxamide.

In some embodiments, the ingestible medicament may be an ingestible medicament for treatment of an ailment of the GI tract, which may be, or include, at least one of:
- at least one osmotic agent, such as magnesium citrate, magnesium hydroxide, polyethylene glycol, or sodium phosphate;
- MiraLAX®;
- at least one contraction stimulating agent, such as bisacodyl or senna;
- at least one of Correctol, Ducodyl, Dulcolax, Senexon, and Senokot;
- at least one stool softening agent, such as docusate sodium;
- Colace;
- Linaclotide;
- Lactulose;
- lubiprostone;
- plecanatide;
- prucaltride; and
- loperamide or bismuth subsalicylate.

In some embodiments, the ingestible medicament may be ingested directly, for example by ingesting a tablet, capsule, liqui-gel capsule, chewable tablet, syrup, or any other form of dosage including the medicament. In such embodiments, the ingestible medicament is considered to be exposed to fluids of the gastrointestinal tract from the moment of ingestion thereof.

In some embodiments, the vibrating ingestible capsule is devoid of a compartment or chamber in which the ingestible medicament may be disposed, for example during ingestion of the capsule.

In some embodiments, the ingestible medicament may be ingested within a medicament delivery capsule, adapted to deliver the medicament to a specific location in the gastrointestinal tract. In such embodiments, the ingestible medicament is considered to be exposed to fluids of the gastrointestinal tract from a time when the fluids of the gastrointestinal tract an enter a portion of the medicament delivery capsule holding the ingestible medicament, or from a time that the ingestible medicament is released from the medicament delivery capsule into the gastrointestinal tract.

Examples of such medicament delivery capsules are described in:
- U.S. Pat. Nos. 5,170,801; 6,632,216; 6,776,165; 6,929,363; 8,202,697; 8,518,022; 8,597,278; and 8,771,730;
- U.S. Patent Application Publication Numbers 2004/0253304; 2004/0267240; 2005/0058701; 2005/0148847; 2008/0275430; 2009/0306633; 2010/0049012; and 2016/0136104.
- PCT Patent Application Publication Numbers WO2006/025013; WO2008/012700; and WO 2009/063375;
- all of which are incorporated by reference for all purposes as if fully set forth herein.

At step 206, the vibrating gastrointestinal capsule is ingested by the subject.

While the ingestible medicament and the vibrating gastrointestinal capsule may be ingested at the same time, or within 0-30 minutes of each other, no order of action is implied by FIG. 2, and the capsule may be ingested prior to the medicament.

In some embodiments, the vibrating gastrointestinal capsule functions also as a medicament delivery system for delivery of the ingestible medicament and delivers the medicament to a specific area or location in the gastrointestinal tract of the subject. In such embodiments, the subject ingests a single capsule, the vibrating ingestible capsule, thereby fulfilling steps 204 and 206 of the method.

As shown, step 208A includes controlling at least one of a time of ingesting the vibrating gastrointestinal capsule and a timing of said vibration mode of operation (e.g., when the vibration mode is initiated, a duration of the vibration mode, etc.) to at least partially transpire within at an absorption time period of the ingestible medicament within the gastrointestinal tract of the subject. Typically, the absorption time period is an estimated absorption time period, as defined herein. In some cases, an actual absorption time period may be determined, again, as defined herein.

Additionally or alternatively, the method may include controlling at least one of a timing of ingesting the vibrating gastrointestinal capsule and a timing of said vibration mode of operation such that the vibration mode at least partially transpires within a particular time period with respect to the ingesting of the ingestible medicament (step 208B).

The particular time period may be within 5 hours, within 4 hours, within 3.5 hours, within 3 hours, or within 2.5 hours of the ingesting of the ingestible medicament, and more typically, within 2 hours, within 1.5 hours, within 1 hour, or within 0.5 hours thereof.

In some embodiments, the method may include controlling at least one of a timing of ingesting the vibrating gastrointestinal capsule and a timing of said vibration mode of operation such that said vibration mode at least partially transpires when the capsule is in a region of the gastrointestinal tract in which the medicament is typically absorbed into the bloodstream. The region of the gastrointestinal tract may include one or more of the stomach of the subject, the duodenum of the subject, the small intestine of the subject, the large intestine of the subject, or the colon of the subject.

For example, when cooperating with the medicament levadopa (for treatment of Parkinsonism), which is typically absorbed into the bloodstream through the stomach walls and/or the small intestine walls, the vibration mode at least partially transpires within a time period in which the capsule traverses, or is expected to traverse, the stomach and small intestine.

As another example, when cooperating with the medicament Linzess® (for treatment of constipation), which is typically absorbed into the bloodstream through the stomach walls and/or the small intestine walls, the vibration mode at least partially transpires within a time period in which the capsule traverses, or is expected to traverse, the stomach and small intestine.

In some embodiments, and as described in further detail herein, the method may include transitioning the capsule (from an inoperative state) to an operative state.

The capsule may be pre-programmed with a vibration protocol. This protocol may include, by way of example, a particular or pre-determined activation time following ingestion, in which the capsule is transitioned from an inoperative state to an operative state.

Alternatively or additionally, the capsule may receive an activation input in an active fashion (e.g., from an external controller via RF) or in a passive fashion (e.g., a signal from a sensor to the on-board controller). It will be appreciated that step 202, in which the vibrating ingestible capsule is transitioned from the inoperative state to the operative state, may be performed after ingestion of the capsule by the subject (e.g., in the case of external control via RF).

In some embodiments, control mechanism 106 may optionally receive a desired vibration protocol for the subject, at an optional step 203.

In some embodiments, providing of the predetermined time(s) at step 202 and/or providing the desired vibration protocol for the subject at step 203 occurs at the time of manufacturing of the capsule, for example by pre-programming the time into the control mechanism.

In some embodiments, providing of the predetermined time(s) at step 202 and/or providing the desired vibration protocol for the subject at step 203 may be effected by a control unit, such as control unit 120 of FIG. 1.

The programming of the vibration protocol may include remotely transmitting the desired vibration protocol from control unit 120 to control mechanism 106, for example using a short-range wireless communication method. In some embodiments, the desired vibration protocol is transmitted as a list of vibration parameters for effecting the vibration protocol. In some embodiments, the desired vibration protocol is transmitted as executable code for effecting the vibration protocol.

As discussed hereinabove, in some embodiments the activation input may be received from the control unit 120 or from sensors within the capsule sensing that the capsule has been ingested or that a user has carried out an activation motion with the capsule.

Substantially as described hereinabove, the vibrating ingestible capsule may be activated prior to the user ingesting the capsule at step 206, for example by a signal from the control unit or by the user carrying out an activation motion. In other embodiments, the activation input is provided at the time of ingestion or immediately thereafter, for example by sensors sensing a change in the environment of the capsule due to its ingestion, as described at length hereinabove. In yet other embodiments, the activation input may be provided remotely when the capsule is already in the body of the subject, for example by remote communication from control module 120.

Following activation of capsule 101, or together therewith, capsule 101 is ingested by the subject, and begins to travel through the gastrointestinal tract of the subject, as evident from step 206.

Operation of vibrating agitation mechanism 104 in the vibrating mode of operation at step 208A or 208B effects vibration of capsule housing 102, as described hereinabove, such that the housing exerts vibrations on the environment surrounding the capsule. The exerted vibration maintains the integrity of capsule housing 102 and of capsule 101. Specifically, vibration of capsule housing 102 may be intended to effect a mechanical stimulation of the wall of the gastrointestinal tract at a time when the ingested medicament may be absorbed, thereby to increase or accelerate the absorption of the ingested medicament into the bloodstream of the subject, for delivery to a target treatment region of the medicament.

For example, the target treatment region of medicaments for treatment of Parkinsonism is in or near the brain, and as such an ingestible medicament for treatment of Parkinsonism, when absorbed to the bloodstream in the gastrointestinal tract, is delivered to the target treatment region away from the gastrointestinal tract.

In some embodiments, an additional step 210 includes controlling the vibrating agitation mechanism of the capsule 101 to also operate in the vibration mode of operation also following the absorption time period of the ingestible medicament, and/or further along the GI tract from the region in which the ingestible medicament is typically absorbed. For example, step 208A may occur when the capsule 101 is located in the stomach of the user, where the ingestible medicament is typically absorbed, and step 210 may occur when capsule 101 is located in the colon of the user, for example to ease constipation symptoms of the user.

In some embodiments, between steps 208A or 208B, in which the capsule is in the vibration mode of operation, and step 210 in which the capsule is again in the vibration mode of operation, control mechanism 106 may control capsule 101 to be in the rest mode of operation at optional step 212. Relating back to the example above, during the time the capsule travels from the stomach of the subject (where it is in the vibration mode of operation—step 208A) to the colon of the subject (where it is in the vibration mode of operation—step 210), the control mechanism controls the capsule to be in the rest mode of operation.

A treatment session as defined in FIG. 2 may be repeatedly administered to the subject as specified in the treatment protocol for the subject. In some embodiments, the treatment protocol includes administering a plurality of treatment sessions to the subject. In some embodiments, the treatment protocol includes administering at least one treatment session to the subject per week, over a treatment period of at least two weeks, at least at least three weeks, at least four weeks, at least five weeks, at least six weeks, or at least eight weeks. In some embodiments, the treatment protocol includes administering 1 to 7 treatment sessions per week, 3 to 14 treatment sessions per two weeks, 2 to 7 treatment sessions per week, 5 to 14 treatment sessions per two weeks, 3 to 7 treatment sessions per week, 7 to 14 treatment sessions per two weeks, 4 to 7 treatment sessions per week, or 5 to 7 treatment sessions per week.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A kit for promoting absorption of an ingested medicament into the bloodstream of a subject, the kit comprising:

a medicament to be ingested, said medicament being absorbable within a target region of the gastrointestinal tract, the target region being selected from the group consisting of the stomach, the small intestine, and the large intestine; and a vibrating ingestible capsule including:

a housing;

a vibrating agitation mechanism having a rest mode of operation and a vibration mode of operation, and adapted such that, in said vibration mode of operation, said housing exerts vibrations on an environment surrounding said vibrating gastrointestinal capsule, wherein, in said vibration mode of operation, said vibrating agitation mechanism is configured to exert said forces on said housing to attain a vibrational frequency within a range of 100 Hz to 500 Hz;

a power supply disposed within said housing and adapted to power said vibrating agitation mechanism; and a control mechanism adapted to activate said vibrating agitation mechanism to be operative in said vibration mode of operation, said control mechanism configured to control a timing or activation delay of said vibration mode of operation such that, when the vibrating ingestible capsule is ingested by the subject, a first occurrence of said vibration mode of operation at least partially transpires in said target region of the gastrointestinal tract of the subject, within at least one of an estimated absorption time period and an actual absorption time period of said ingested medicament within said target region, so as to increase absorption of said ingested medicament into the bloodstream of the subject.

2. The kit of claim 1, wherein operation of said vibrating agitation mechanism in said vibration mode of operation maintains the integrity of said housing.

3. The kit of claim 1, wherein operation of said vibrating agitation mechanism in said vibration mode of operation maintains the integrity of said vibrating ingestible capsule.

4. The kit of claim 1, wherein said control mechanism is further adapted to control the timing of said vibration mode of operation such that a second occurrence of said vibration mode of operation transpires while said capsule is within at least one of the large intestine and the colon of the subject.

5. The kit of claim 4, wherein said control mechanism is further adapted to control the timing of said vibration mode of operation such that between said first and said second occurrences of said vibration mode of operation, said vibration agitation mechanism is in the rest mode of operation.

6. The kit of claim 1, wherein said vibrating ingestible capsule is devoid of a chamber for containing said medicament to be ingested.

7. The kit of claim 1, wherein said target region is the stomach, and wherein said control mechanism is adapted to activate said vibrating agitation mechanism such that said first occurrence of said vibration mode of operation at least partially transpires in the stomach.

8. The kit of claim 1, wherein said target region is in the small intestine, and wherein said control mechanism is adapted to activate said vibrating agitation mechanism such that said first occurrence of said vibration mode of operation at least partially transpires in the small intestine.

9. The kit of claim 1, wherein said vibrating agitation mechanism is adapted to be in said rest mode of operation prior to said first occurrence of said vibration mode of operation.

10. The kit of claim 1, wherein, in said vibrating mode of operation, said vibrating agitation mechanism is adapted to have a plurality of vibration cycles, where each cycle includes a vibration duration followed by a repose duration.

11. The kit of claim 1, wherein the medicament to be ingested is physically separate from the vibrating ingestible capsule.

12. A method of using the kit of claim 1, by a subject, the method comprising:

a. ingesting said medicament to be ingested; and b. ingesting said vibrating ingestible capsule, wherein the control mechanism of the vibrating ingestible capsule activates said vibrating agitation mechanism to be operative in said vibration mode of operation such that the first occurrence of said vibration mode of operation at least partially transpires in said target region, within the at least one of an estimated absorption time period and an actual absorption time period of said medicament within said target region, thereby to increase absorption of the medicament into the bloodstream of the subject.

13. A kit for promoting absorption of an ingested medicament into the bloodstream of a subject, the kit comprising:

a medicament to be ingested, said medicament being absorbable within a target region of the gastrointestinal tract, the target region being selected from the group consisting of the stomach, the small intestine, and the large intestine; and a vibrating ingestible capsule, physically separate from said medicament to be ingested, said vibrating ingestible capsule including:

a housing;

a vibrating agitation mechanism having a rest mode of operation and a vibration mode of operation, and adapted such that, in said vibration mode of operation, said housing exerts vibrations on an environment surrounding said vibrating gastrointestinal capsule, wherein, in said vibration mode of operation, said vibrating agitation mechanism is configured to exert said forces on said housing to attain a vibrational frequency within a range of 100 Hz to 500 Hz;

a power supply disposed within said housing and adapted to power said vibrating agitation mechanism; and a control mechanism adapted to activate said vibrating agitation mechanism to be operative in said vibration mode of operation, said control mechanism configured to control a timing or activation delay of said vibration mode of operation such that, when the vibrating ingestible capsule is ingested by the subject, a first occurrence of said vibration mode of operation at least partially transpires in said target region of the gastrointestinal tract of the subject, within at least one of an estimated absorption time period and an actual absorption time period of said ingested medicament within said target region, so as to increase absorption of said ingested medicament into the bloodstream of the subject, wherein said vibrating agitation mechanism is adapted to be in said rest mode of operation prior to said first occurrence of said vibration mode of operation.

*    *    *    *    *